United States Patent [19]

Kwiatek et al.

[11] 4,415,475

[45] Nov. 15, 1983

[54] MIXED METAL OXIDE CATALYST CONTAINING TITANIUM, BORON AND MOLYBDENUM VALUES

[75] Inventors: Thomas S. Brima, Cincinnati, Ohio

[73] Assignee: National Distillers and Chemical Corporation, New York, N.Y.

[21] Appl. No.: 390,142

[22] Filed: Jun. 18, 1982

Related U.S. Application Data

[62] Division of Ser. No. 280,172, Jul. 2, 1981, Pat. No. 4,358,601.

[51] Int. Cl.³ .............................................. B01J 21/02
[52] U.S. Cl. .................................................... 502/206
[58] Field of Search ........................................ 252/432

[56] References Cited

U.S. PATENT DOCUMENTS

| | | | |
|---|---|---|---|
| 2,446,619 | 8/1948 | Stewart et al. | 252/432 X |
| 2,507,510 | 5/1950 | Frankenberg | 252/432 X |
| 3,297,587 | 1/1967 | Scherberg et al. | 252/432 |
| 3,458,532 | 7/1969 | Hayden | 562/577 X |
| 3,746,657 | 7/1973 | Miller et al. | 252/432 X |
| 3,796,671 | 3/1974 | Gleim | 252/432 |
| 4,119,642 | 10/1978 | Larock | 549/265 |
| 4,182,907 | 1/1980 | Grosselli et al. | 252/432 X |

FOREIGN PATENT DOCUMENTS

| | | | |
|---|---|---|---|
| 53-30475 | 3/1978 | Japan | 252/432 |
| 54-149390 | 11/1979 | Japan | 252/432 |

*Primary Examiner*—William G. Wright
*Attorney, Agent, or Firm*—Kenneth D. Tremain

[57] ABSTRACT

A process for preparing 2-butenolide, a useful product for the manufacture of gamma-butyrolactone, is disclosed which comprises reacting furan with oxygen in the presence of a catalytically effective amount of a catalyst comprising a mixed metal oxide containing titanium, boron and molybdenum.

10 Claims, No Drawings

MIXED METAL OXIDE CATALYST CONTAINING TITANIUM, BORON AND MOLYBDENUM VALUES

This is a division of application Ser. No. 280,172, filed July 2, 1981, now U.S. Pat. No. 4,358,601, and a continuation-in-part of application Ser. No. 280,168, filed July 2, 1981, now U.S. Pat. No. 4,356,310.

BACKGROUND OF THE INVENTION

1. Field of the Invention

This invention relates to processes for preparing lactones and, more particularly, to processes for preparing 2-butenolide (also known as gamma-crotonolactone) by the catalyzed vapor phase reaction of furan and oxygen.

2. Description of the Prior Art

2-Butenolide, an unsaturated lactone, readily undergoes catalytic hydrogenation in a known and conventional matter to provide the saturated lactone, gamma-butyrolactone, according to the equation:

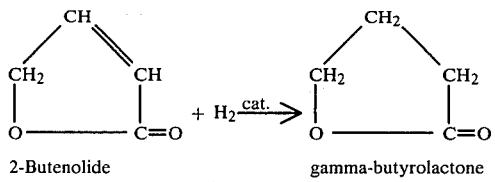

Assuming the availability of a relatively low cost source of 2-butenolide, the foregoing synthesis of gamma-butyrolactone would be a commercially attractive route to the production of the latter compound, an important intermediate for the manufacture of butyric and succinic acids, 1,4-butanediol and other industrially important products.

While processes for the preparation of unsaturated lactones are known (e.g., the process of U.S. Pat. No. 3,458,532 to Hayden which provides unsaturated lactones by the carbonylation of ethylene or propylene in the presence of a palladium salt as catalyst and the process of U.S. Pat. No. 4,119,642 to Larock which provides beta-halobutenolides by the carbonylation of vinylmercurials in the presence of a basic inorganic salt), a convenient one-step synthesis of 2-butenolide employing relatively abundant, low cost and readily available raw materials has heretofore not been made available.

SUMMARY OF THE INVENTION

It has now been discovered that 2-butenolide can be readily and conveniently prepared by the vapor phase reaction of furan with oxygen in the presence of a catalytically effective amount of a substantially water-insoluble mixed metal oxide catalyst containing the metallic elements titanium, boron and molybdenum.

The term "mixed metal oxide" as used herein is to be understood in its art-recognized sense, i.e., as a combination of individual metal oxides which are more intimately associated with each other than the individual metal oxides of a mere mechanical mixture (viz. U.S. Pat. No. 2,769,847 to Robinson).

DESCRIPTION OF THE PREFERRED EMBODIMENTS

The starting furan herein can be substantially pure but, more usually, will be of industrial or commercial quality, i.e., in admixture with minor amounts of one or more impurities.

The source of oxygen herein is not critical and includes pure oxygen, enriched air and atmospheric air, the latter being preferred for reasons of economy and convenience. By way of promoting conversion of furan to 2-butenolide, it is advantageous to use a large stoichiometric excess of oxygen, e.g., from about 1.5 to 5 times the theoretical amount needed, care, of course, being observed to avoid an explosive mixture.

The reaction herein most readily occurs in the vapor phase and at elevated temperatures. Pressures of up to about 5,000 psig and preferably, pressures ranging from atmospheric to 1,000 psig, can be used with good results. Temperatures can be widely varied and in general will be in the range of from about 100° C. to about 500° C., and preferably from about 200° C. to about 400° C. Partial pressures of furan can vary widely with relatively high partial pressures of furan favoring the production predominantly of 2-butenolide and relatively low partial pressures of this reactant favoring the production of a mixture of 2-butenolide and maleic acid, the latter also being an industrially important compound. Such mixtures can, of course, be readily resolved into their components employing routine procedures well known in the art.

The reaction can be carried out on a batch or continuous basis, the latter being more readily suitable to low-cost operation. The process herein contemplates the use of known and conventional oxidation-resistant apparatus which is commercially available from numerous sources.

The mixed metal oxide catalyst herein must contain titanium, boron and molybdenum values and optionally can be supported upon an insert inorganic carrier such as silica, silica gel, titania, zirconia, alumina, and the like. Mixed metal oxides having the elements of titanium, boron and molybdenum in which the atomic ratio of titanium to molybdenum is from about 0.1:1 to about 10:1 and preferably from about 0.2:1 to about 5:1, and the atomic ratio of boron to molybdenum is from about 0.5:1 to about 50:1 and preferably from about 1:1 to about 20:1 are advantageously employed herein.

The amount of catalyst employed can vary over fairly wide limits and the level of catalyst selected will be such as to provide a suitable range of superficial contact time, e.g., from a few seconds to a few minutes or more, under the prevailing reaction conditions. The relationship between superficial contact time, catalyst volume and reaction conditions is given by the equation:

$$\text{Superficial Contact Time} = \frac{\text{Volume Catalyst}}{\text{Total Vol. feed gases} \times \frac{T_1}{T_2} \times \frac{P_1}{P_2}}$$

Thus, for example, given an adjusted flow rate of air at 350+ C. of 20.07 liters, furan feed rate of 3 ml/hr (2.80 /hr), a volume of furan at STP of 0.923 liters/hr and a total gas flow rate at 350° C. of 22.176 liters/hour, the superficial contact time is calculated to be 8.12 seconds.

A variety of procedures can be used to prepare the catalyst used in the process of this invention. In accordance with one procedure of preparing mixed metal oxide catalyst, a titanium halide such as titanium tetrachloride is reacted with ammonium heptamolybdate and the resulting product is then reacted with boric acid or alkyl borate to provide a solid which, after being optionally deposited upon a carrier such as any of those aforementioned, is calcined, preferably in an inert or oxygen-containing atmosphere and preferably below about 500° C., to yield the desired catalyst.

In yet another procedure to provide mixed metal oxide catalyst, a titanium halide such as titanium tetrachloride is reacted with boric acid or an alkyl borate to provide a titanium borate which is thereafter reacted with ammonium heptamolybdate to provide a solid which, after being optionally deposited upon a carrier such as any of those aforementioned, is calcined, preferably in an inert or oxygen-containing atmosphere and preferably below about 500° C., to yield the desired catalyst.

Copending application Ser. No. 280,168 of Thomas S. Brima, now U.S. Pat. No. 4,356,310, is related to this application. Said application discloses a process for preparing gamma-butyrolactone and butenolide by the reaction of 1,3-butadiene and oxygen employing the same mixed metal oxide catalyst disclosed herein. Said copending application discloses one of the two catalyst preparation procedures disclosed herein, namely a preparation which includes reacting a titanium halide with boric acid or an alkyl borate to provide a titanium borate which is thereafter reacted with ammonium heptamolybdate to provide a titanium, boron and molybdenum-containing solid. The entire contents of said application, now U.S. Pat. 4,356,310, are incorporated herein by reference.

EXAMPLE 1

Water was added to 44.1 g ammonium heptamolybdate tetrahydrate in an amount sufficient to dissolve it. This solution was added to an aqueous ammonia solution (a mixture of 440 ml 28% NH$_4$OH and 250 ml water), and to the solution so-formed was added 11 ml titanium tetrachloride over a 30 minute period. After the reaction subsided, 250 ml water was added to the resulting mixture. Alumina (30 g) was then added, followed by 250 ml 28% aqueous ammonia. The mixture was then heated with stirring for 45 minutes. The pH of the solution was adjusted to 1.5 with hydrochloric acid, the mixture was stirred for 5 minutes and 150 ml of an aqueous solution (2 g/1,000 ml) of flocculating agent, Jaguar C-13 (Stein-Hall) was added.

After settling overnight, the clear liquor was siphoned off, the residue was washed with water (about 1,500 ml) and finally separated by filtration. A solution of 165 g boric acid in methanol was blended with the semi-dry filter cake to form a smooth paste from which the methanol was then removed by evaporation. The resultant solid was dried overnight in an air oven at 110° C. to obtain 249 g of a blue powder which was then pelletized. The pellets after calcining at 550° C. for 7 hours provided the catalyst employed in the reactions described in Examples 3 and 4.

EXAMPLE 2

To a well-stirred suspension of boric acid (110 g, 178 m) in toluene (150 ml) was added titanium tetrachloride (133 ml, 230 g, 1.21 m) at room temperature. Stirring was continued until hydrochloric acid evolution was negligible (16 hours). The titanium borate formed was removed by filtration and dried in vacuo. The yield of 206 g indicated that not all of the chlorine had been eliminated.

A mixture of this titanium borate (43 g) and ammonium heptamolybdate (16.25 g, 0.013 m) (0.092 g atoms Mo) was ground to a fine powder and refluxed in absolute ethanol (50 ml). The suspension turned green after 45 minutes and blue on further refluxing (1½ hours). The solvent was then removed by evaporation, and the solid residue was dried at 110° C. for 2 hours. The green solid was then ground, blended with titania (50 g), pelletized and calcined at 400° C. for 16 hours. The finished catalyst contained 51.1% Ti, 3.4% B and 11.6% Mo as determined by atomic absorption. The catalyst was employed in the reaction described in Example 5.

EXAMPLE 3

Oxidation of furan was carried out in a stainless steel tubular reactor in which a 75 ml preheater zone, packed with chemically resistant glass bead is separated from a 50 ml catalyst chamber, packed with catalyst described in Example 1, by a perforated plate.

Furan was introduced at a rate of 3 ml/hour into the preheater chamber, held at a temperature of 300° C., where it was mixed with air fed at a rate of 160 ml/minute. The mixed vapors then passed through the catalyst bed, held at a temperature of 350° C., into an ice-water cooled trap followed by a dry-ice-acetone cooled trap.

The liquid products so-obtained in 62 minutes reaction time were separated by gas-liquid chromatography [carbowax 20 M column at 160° C.]. A 36% conversion of furan giving 2-butenolide in 60% selectivity was obtained. The 2-butenolide was further characterized by its mass spectrum.

EXAMPLE 4

The procedure of Example 3 was substantially repeated except that furan was fed at a rate of 1 ml/hr and product was collected over a three-hour period. Analysis of the product indicated 64% of the furan was converted to maleic acid (83%) 2-butenolide (8%), acetic acid (7%) and acrylic acid (2%).

EXAMPLE 5

Furan was oxidized to the mixture of products shown below over the mixed metal oxide catalyst of Example 2 employing substantially the same procedure as described in Example 3. The results were as follows:

| Reaction Temp, °C. | Feed Rates Furan (g/h) | Feed Rates Air (l/h) | % Conversion | Selectivity Wt. % Gamma-Crotonolactone | Selectivity Wt. % Maleic Acid + Maleic Anhydride |
|---|---|---|---|---|---|
| 260 | 3.8 | 11.85 | 2 | 82 | 5 |
| 270 | 3.25 | 11.85 | 29.2 | 49 | 40 |
| 295 | 2.85 | 11.85 | 63.2 | 0 | 60 |

What is claimed is:

1. A catalyst consisting essentially of a mixed metal oxide of titanium, boron and molybdenum values prepared by the process which comprises reacting titanium halide with ammonium heptamolybdate, and reacting the resulting product with boric acid or alkyl borate and thereafter calcining the recovered solid in an inert or oxygen-containing atmosphere.

2. The catalyst of claim 1 wherein the atomic ratio of titanium to molybdenum is from about 0.1:1 to about 10:1.

3. The catalyst of claim 1 wherein the atomic ratio of titanium to molybdenum is from about 0.2:1 to about 5:1.

4. The catalyst of claim 1 wherein the atomic ratio of boron to molybdenum is from about 0.5:1 to about 50:1.

5. The catalyst of claim 1 wherein the atomic ratio of boron to molybdenum is from about 1:1 to about 20:1.

6. A catalyst consisting essentially of a mixed metal oxide of titanium, boron and molybdenum values prepared by the process which comprises reacting a titanium halide with boric acid or alkyl borate to provide a titanium borate, and reacting said titanium borate with ammonium heptamolybdate and thereafter calcining the recovered solid in an inert or oxygen-containing atmosphere.

7. The catalyst of claim 6 wherein the atomic ratio of titanium to molybdenum is from about 0.1:1 to about 10:1.

8. The catalyst of claim 6 wherein the atomic ratio of titanium to molybdenum is from about 0.2:1 to about 5:1.

9. The catalyst of claim 6 wherein the atomic ratio of boron to molybdenum is from about 0.5:1 to about 50:1.

10. The catalyst of claim 6 wherein the atomic ratio of boron to molybdenum is from about 1:1 to about 20:1.

* * * * *